United States Patent
Koeth et al.

(10) Patent No.: US 10,384,021 B2
(45) Date of Patent: Aug. 20, 2019

(54) PRESSURE-MAINTAINING SMOKE EVACUATION IN AN INSUFFLATOR

(71) Applicant: W.O.M. World of Medicine GmbH, Berlin (DE)

(72) Inventors: Yves Koeth, Berlin (DE); Sebastian Stegemann, Berlin (DE)

(73) Assignee: W.O.M. WORLD OF MEDICINE GMBH, Berlin (DE)

( * ) Notice: Subject to any disclaimer, the term of this patent is extended or adjusted under 35 U.S.C. 154(b) by 251 days.

(21) Appl. No.: 15/024,947

(22) PCT Filed: Sep. 26, 2014

(86) PCT No.: PCT/DE2014/000482
§ 371 (c)(1),
(2) Date: Jun. 22, 2016

(87) PCT Pub. No.: WO2015/043570
PCT Pub. Date: Apr. 2, 2015

(65) Prior Publication Data
US 2016/0317764 A1  Nov. 3, 2016

(30) Foreign Application Priority Data
Sep. 27, 2013 (DE) .................. 10 2013 016 063

(51) Int. Cl.
*A61M 13/00* (2006.01)
*A61M 16/16* (2006.01)
(Continued)

(52) U.S. Cl.
CPC ....... *A61M 13/003* (2013.01); *A61B 18/1482* (2013.01); *A61B 18/20* (2013.01); *A61B 2218/008* (2013.01); *A61M 16/16* (2013.01);
*A61M 16/203* (2014.02); *A61M 2205/07* (2013.01); *A61M 2205/3334* (2013.01); *A61M 2205/3337* (2013.01);
(Continued)

(58) Field of Classification Search
CPC .............. A61M 13/003; A61M 16/203; A61M 2205/07; A61M 2205/3334; A61M 2205/3344; A61B 18/1482
See application file for complete search history.

(56) References Cited

U.S. PATENT DOCUMENTS

| 4,735,603 A | 4/1988 | Goodson et al. |
| 4,836,187 A | 6/1989 | Iwakoshi et al. |

(Continued)

FOREIGN PATENT DOCUMENTS

| DE | 3922746 C1 | 8/1990 |
| DE | 4219859 A1 | 12/1993 |

(Continued)

OTHER PUBLICATIONS

International Search Report dated Jan. 23, 2015 issued in connection with corresponding International Application No. PCT/DE2014/000482 (3 pages total).

*Primary Examiner* — Bradley J Osinski
(74) *Attorney, Agent, or Firm* — Stuart H. Mayer; Mayer & Williams PC

(57) ABSTRACT

The present invention relates to an insufflator with a flue gas extraction, which is configured such that the abdominal pressure remains substantially constant during the extraction process.

10 Claims, 3 Drawing Sheets

(51) Int. Cl.
  *A61M 16/20* (2006.01)
  *A61B 18/14* (2006.01)
  *A61B 18/20* (2006.01)

(52) U.S. Cl.
  CPC . *A61M 2205/3344* (2013.01); *A61M 2205/50* (2013.01); *A61M 2205/75* (2013.01)

(56) References Cited

U.S. PATENT DOCUMENTS

| | | | |
|---|---|---|---|
| 4,971,034 A | | 11/1990 | Doi et al. |
| 5,411,474 A | * | 5/1995 | Ott .................. A61M 13/003 600/560 |
| 6,592,543 B1 | | 7/2003 | Wortrich et al. |
| 7,806,850 B2 | * | 10/2010 | Williams, Jr. ...... A61M 13/003 604/26 |

FOREIGN PATENT DOCUMENTS

| | | |
|---|---|---|
| WO | 2004/009167 A1 | 1/2004 |
| WO | 200723565 | 11/2007 |
| WO | 2011/041387 A1 | 4/2011 |
| WO | 2012/012379 A1 | 1/2012 |
| WO | 2014/111083 | 7/2014 |
| WO | 2014/111084 | 7/2014 |

* cited by examiner

PRESSURE-MAINTAINING SMOKE EVACUATION IN AN INSUFFLATOR

The present invention relates to an insufflator with a flue gas extraction, which is configured such that the abdominal pressure remains substantially constant during the extraction process. The priority of the German application DE 102013016063.4 (date of filing 27 Sep. 2014) is claimed.

BACKGROUND AND PRIOR ART

In the field of minimally invasive surgery, for example diagnostic or therapeutic laparoscopy, an overpressure is generated in the abdomen by means of introduced gases (e.g., medical carbon dioxide ($CO_2$)), said overpressure expanding the abdomen, in order that sufficient space is available for the visual inspection or the therapeutic procedure. For this purpose, so-called insufflators are used, which build up, by means of an adjusted gas flow, a controlled pressure in the abdomen. By a series of safety devices it is secured that the abdominal pressure is kept within limits, so that no tissue is damaged.

In the field of minimally invasive surgery, frequently electro-surgical devices or also lasers are used, the application of which will generate smoke in the abdomen. This smoke does not only obstruct the view, but contains contaminants (in the form of gases, droplets, and/or particles), so that this smoke has to be removed from the abdomen. A solution of this problem is that a simple outlet is formed, through which the flue gases exit from the body. A possibility of implementation for this is shown in U.S. Pat. No. 6,592,543. The extraction process is manually controlled by the surgeon by opening the valve at the trocar. However, current systems frequently produce larger amounts of smoke than at the date of filing of U.S. Pat. No. 6,592,543, so that the solution presented there cannot be used anymore today.

An improvement of such passive systems is achieved by providing an extraction device that can actively extract the gas in the abdomen including the smoke particles. Such a system is described, for instance, in U.S. Pat. No. 5,199,944. Therein, there is a problem that in a too strong extraction process of the flue gases, the pressure in the abdomen will decrease, so that the abdomen may collapse. The treating physician will then have to wait with the continuation of the surgery, until a sufficient pressure has built up again in the abdomen. It is easily understandable that such procedures have enormous disadvantages. On the other hand, in a too weak extraction process, it will not be effective enough, so that the surgeon is hindered by the poor vision, and the surgery will be prolonged. An alternative of this procedure is to re-supply the extracted gas to the patient (circulation). Such a system is described in the U.S. Pat. No. 4,735,603. In this embodiment, too, there is a problem that with too high extraction rate the abdominal pressure will decrease.

With high extraction capacity, the system pressure on the supply line will strongly increase. Depending on how narrow the connected instrument is, the pressure may increase to a higher or lower extent. In either case, at a certain pressure limit the supply line will open the safety valve within the supply line, and thus a pressure drop will be caused. Furthermore, the insufflator cannot supply additional carbon dioxide anymore, in order to compensate for likely existing leakages.

For an extraction process both with and without circulation, there is a problem that the extraction capacity under the actual conditions needs to be adjusted to the surgery. As described, the used instruments, but also the actual leakage rates at the abdomen play an important role here.

It is further state of the art that the surgeon is offered different stages for the extraction capacity at the device (for instance: low/medium/high). The surgeon is therefore responsible to decide the optimum extraction stage. Should the extraction capacity be adjusted too high, the insufflator cannot maintain the abdominal pressure. The surgeon will usually find out about that only when the pressure has already significantly decreased. Furthermore, it is difficult for the surgeon to find out beforehand that a higher extraction capacity is also possible. Possibly, the surgeon will then not select the higher extraction capacity, in order not to risk such a pressure drop.

There is therefore a need of a device for minimally invasive surgery, in particular laparoscopy, that allows to determine and to adjust the highest possible extraction rate for flue gases from the treatment space (in particular the abdomen), so that no significant pressure drop will occur in the mentioned volume. It is intended to be able to use the trocars available on the market. The solution of the problem is secured by the device according to the invention described in the following.

SOLUTION OF THE PROBLEM

Figure 1:
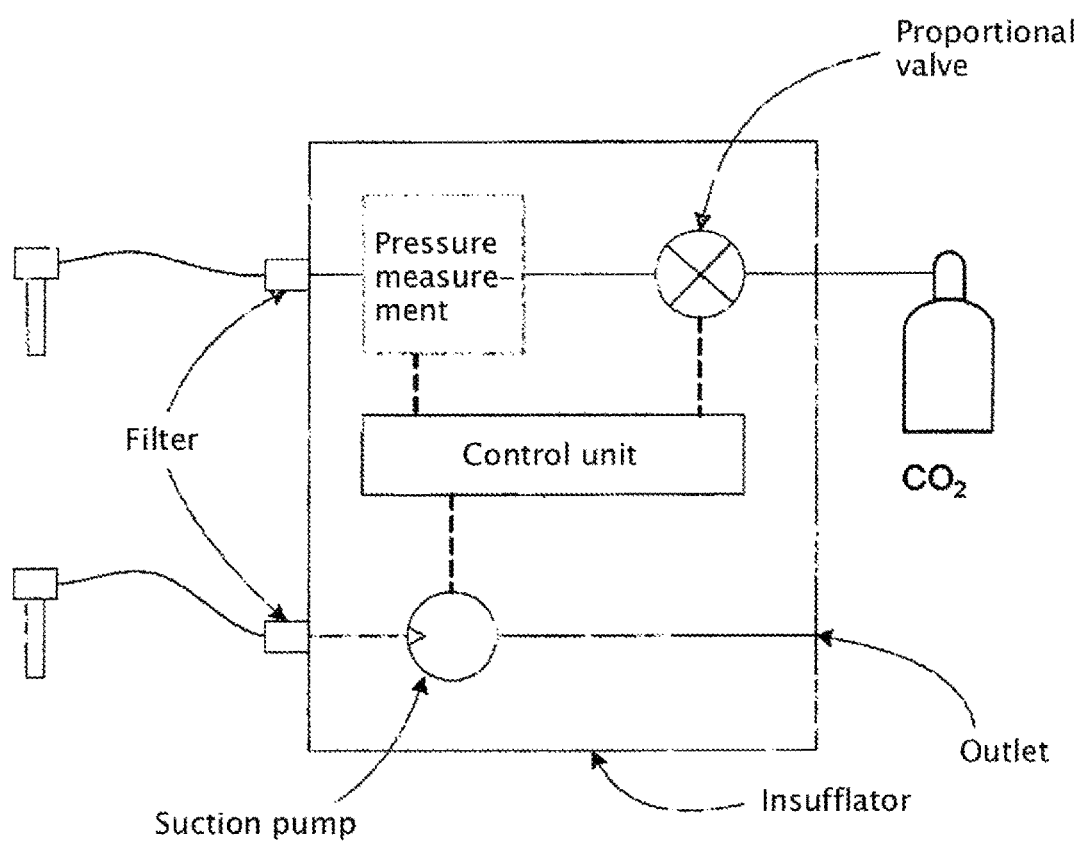
FIG. 1 shows an insufflator with an integrated suction pump.

The solution of the problem is achieved by the subject matter of the patent claims, namely an insufflator with an integrated suction pump. Such a pump is exemplarily shown in FIG. 1. The insufflator includes, first, a usual connection to a compressed gas bottle with a gas, which is suitable for medical purposes, e.g., carbon dioxide. First, the gas is supplied via a proportional valve and a sterile hose to a trocar. Within the insufflator, the pressure as well as the gas in the line is measured. Optionally, a filter is provided that traps particles.

A second trocar is connected to a suction pump integrated in the insufflator. Optionally, again, a filter is provided that can absorb the particles, droplets, and/or poisonous gases. The pumped-off insufflation gas can then be discharged into the atmosphere. The insufflator is controlled through a switching unit (control circuit). The latter adjusts in particular the capacity of the suction pump in an electronic way.

The present invention relates, therefore, to an insufflator for minimally invasive surgery, comprising
a) a gas connection with a proportional valve,
b) a supply line with pressure measurement, filter, and connection to a first trocar,
c) a second trocar with extraction hose and filter, connected to an extraction device with an adjustable extraction capacity,
d) an electronic control unit, characterized by that the electronic control unit adjusts the extraction device in dependence on the pressure in the supply line.

In a particular embodiment of the invention, the insufflator is characterized by that the electronic control unit decreases the extraction rate by control of the extraction device, when the pressure in the supply line exceeds a certain threshold value,
and/or that the electronic control unit increases the extraction rate by control of the extraction device, when the pressure in the supply line falls below a certain threshold value.

The threshold value for decreasing the extraction rate for the pressure in the supply line may for instance be between 60 and 80 mm Hg. The threshold value for increasing the extraction rate for the pressure in the supply line may for instance be between 0 and 50 mm Hg. In particular embodiments of the invention, the threshold values at the insufflator are adjustable.

The maximum flow rate of the insufflator is essentially determined by the instruments connected to the insufflation hose. When using a small or narrow trocar in combination with a large instrument, the maximum insufflation capacity can be 4-6 l/min or less. When using large trocars, the maximum insufflation capacity may be 15-20 l/min or even more.

The insufflator adjusts the volume to be refilled according to the respective need. Of course, for safety reasons already, a maximum pressure is defined in the supply hose that must not be exceeded. This maximum pressure limits the maximum gas flow.

The need of refilling carbon dioxide is caused by permanent and short-time leakages. The trocars employed in the patient have, due to their design, minimum leakages. Furthermore, the active flue gas extraction can so to speak be considered as a permanent leakage that has to be compensated for by the insufflator.

When, for instance, intra-surgically an extraction process with a flow rate of 4 l/min. is present, and a system-due leakage of 3 l/min. exists, then the insufflator has to adjust a flow of ~7 l/min in the supply line. For achieving the target flow, the insufflator has to increase the pressure in the supply hose until either the flow is obtained, or the maximum allowable pressure was achieved. When the maximum pressure is achieved, before the target flow was obtained, the leakage cannot be compensated for by the insufflator. If this condition persists for a longer time, the abdominal pressure would drop. For this reason, in this case, the insufflator has to reduce the extraction capacity.

When, however, sufficient capacity exists in the hose or the instrument, the required flow of 7 l/min. can be adjusted, without the maximum pressure being reached. In this case, the extraction capacity may even be further increased.

The obtained pressure in the supply hose compared to the maximum pressure during insufflation is thus a measure indicating the capacity still available in the hose or the instrument.

The adjustment of the capacity can be performed by means of the ratio described above of obtained driver pressure and maximum driver pressure. When doing this, the input voltage of the pump can directly be varied.

As a result, the capacity of the flue gas extraction is adjusted or optimized to the actual conditions of the insufflation capacity. Thus, the maximum extraction capacity is adjusted, without the patient pressure being changed.

The maximum driver pressure of the device according to the invention is usually 80 mm Hg.

Alternative Embodiments

Figure 2:
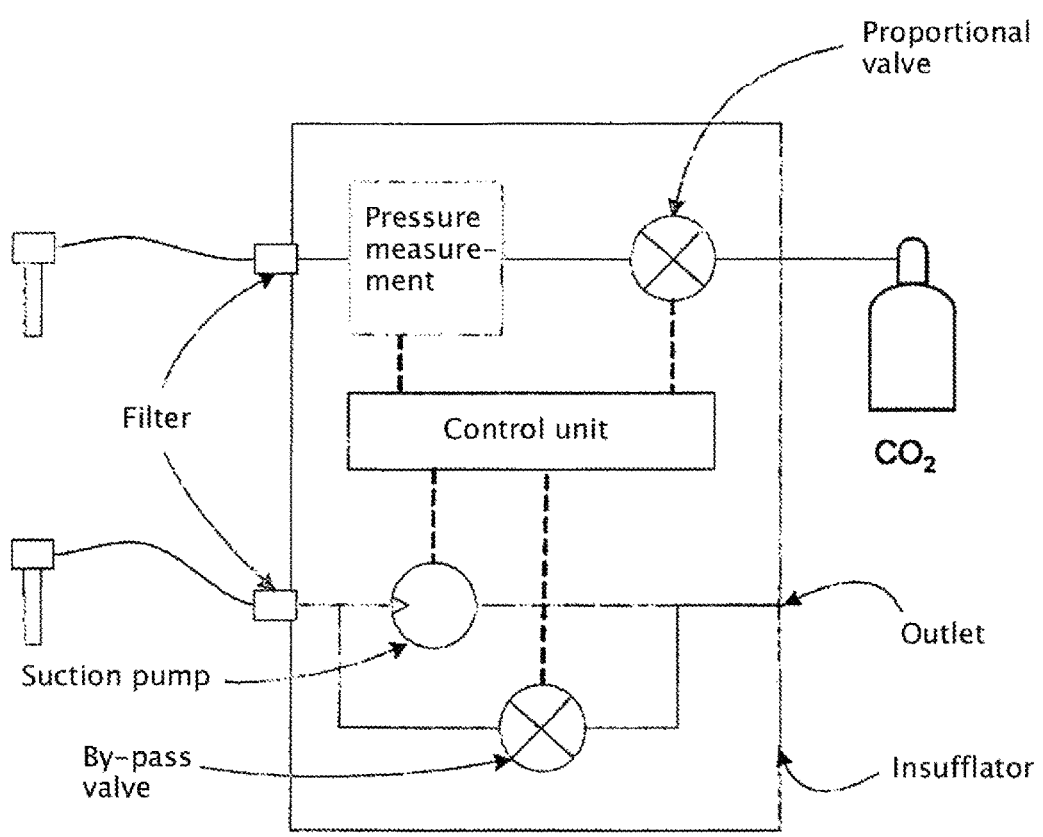
FIG. 2 shows an insufflator with an integrated suction pump, and wherein the suction pump can be controlled through a by-pass valve.

The man skilled in the art will, based on the present description, may be able to implement the basic idea of the invention with other means, too. For instance, the suction pump can be controlled through a by-pass valve (FIG. 2). For this purpose, for instance, the pump can be adjusted to a certain capacity, which is essentially constant, and the adjustment of the capacity is then made through the by-pass valve.

Figure 3:
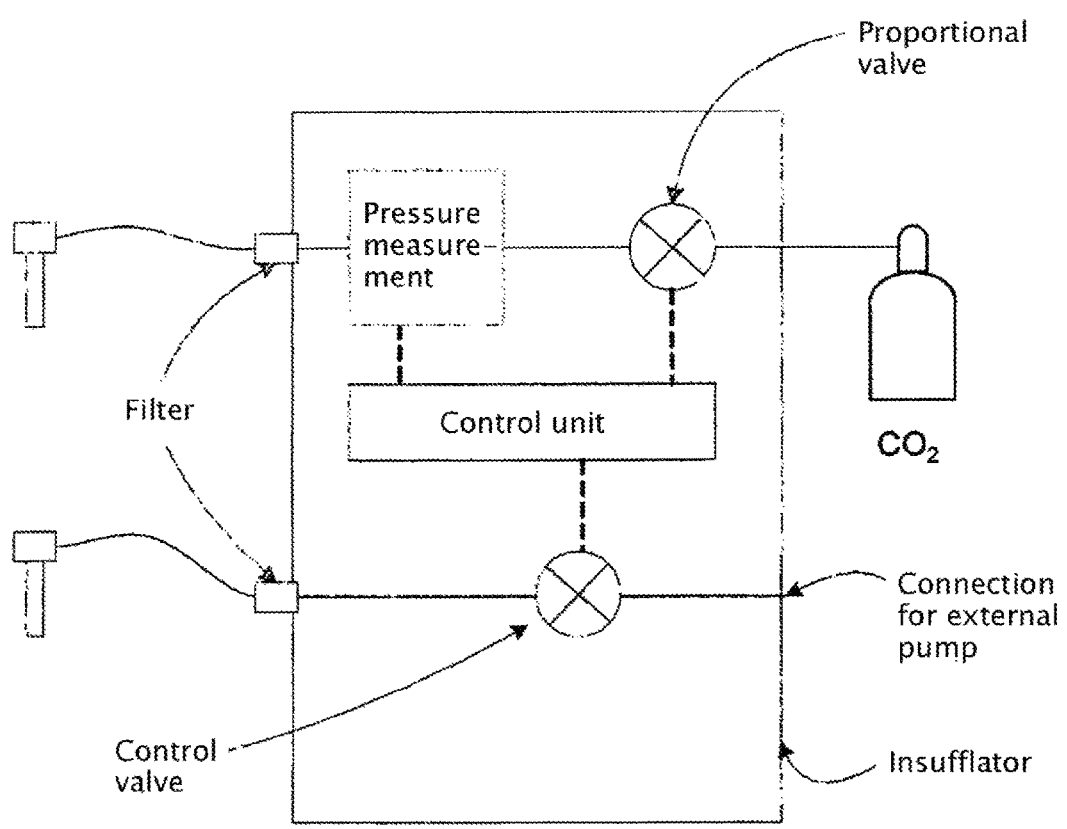
FIG. 3 shows that a control valve may be placed directly in the extraction line of the insufflator.

Furthermore, alternatively, a control valve may also be placed directly in the extraction line (FIG. 3). In this way, external pumps could even be used, for instance the wall extraction system existing in the operating room. The control system of the insufflator will then adjust the extraction capacity through the shown control valve.

In other embodiments of the invention, the gas supply line from the insufflator to the patient may also be heatable, for instance through a hose as described in WO 2014/111084. Alternatively, the gas supply line from the insufflator to the patient may not only be heatable, but also configured for wetting the gas, for instance through a hose, as described in WO 2014/111083.

The invention claimed is:

1. An insufflator for minimally invasive surgery, comprising
   a) a gas connection with a proportional valve,
   b) a supply line with a pressure measurement, filter, and connection to a first trocar,
   c) a second trocar with an extraction hose and filter, connected to an extraction device with an adjustable extraction capacity for extracting insufflation gas such that all insufflation gas that is extracted from a body cavity is always discharged to the atmosphere, and
   d) an electronic control unit,
   wherein the electronic control unit adjusts the extraction device in dependence on the pressure in the supply line.

2. The insufflator of claim 1, wherein the electronic control unit decreases the extraction rate by control of the extraction device, when the pressure in the supply line exceeds a certain threshold value,
   and/or
   that the electronic control unit increases the extraction rate by control of the extraction device, when the pressure in the supply line falls below a certain threshold value.

3. The insufflator of claim 2, wherein the threshold value for decreasing the extraction rate for the pressure in the supply line is between 60 and 80 mm Hg.

4. The insufflator of claim 2, wherein the threshold value for increasing the extraction rate for the pressure in the supply line is between 0 and 50 mm Hg.

5. The insufflator of claim 1, wherein the extraction device with an adjustable extraction capacity consists of an adjustable suction pump
   or
   of a suction pump with an adjustable by-pass valve
   or
   of a suction pump with an additional adjustable proportional valve.

6. The insufflator of claim 1, wherein the extraction device with an adjustable extraction capacity is connected to an external pump, and the extraction capacity is controlled through an adjustable valve.

7. The insufflator of claim 1, wherein an insufflation capacity being adjustable between 0 and 50 l/min.

8. The insufflator of claim 7, wherein an extraction capacity being adjustable between 0 and 20 l/min.

9. The insufflator of claim 8, wherein an extraction capacity being adjustable between 0 and 10 l/min.

10. The insufflator of claim 1, wherein a gas heating device is located in the gas supply line.

* * * * *